(12) United States Patent
Hoffman et al.

(10) Patent No.: US 8,147,527 B2
(45) Date of Patent: Apr. 3, 2012

(54) ADJUSTABLE OCCIPITAL PLATE

(75) Inventors: Zachary M. Hoffman, Bloomington, MN (US); Mark A. Myers, Shakopee, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 634 days.

(21) Appl. No.: 11/563,902

(22) Filed: Nov. 28, 2006

(65) Prior Publication Data

US 2008/0125781 A1    May 29, 2008

(51) Int. Cl.
*A61B 17/80* (2006.01)
*A61B 17/58* (2006.01)

(52) U.S. Cl. ........ 606/280; 606/70; 606/291; 623/17.11

(58) Field of Classification Search .............. 606/70–71, 606/280–299; 623/17.11–17.16
See application file for complete search history.

(56) References Cited

U.S. PATENT DOCUMENTS

| | | | |
|---|---|---|---|
| 4,763,644 A | 8/1988 | Webb | |
| 4,805,602 A | 2/1989 | Puno | |
| 4,836,193 A | 6/1989 | Ransford | |
| 4,841,959 A | 6/1989 | Ransford | |
| 4,887,596 A | 12/1989 | Sherman | |
| 4,950,269 A | 8/1990 | Gaines, Jr. | |
| 5,129,388 A | 7/1992 | Vignaud | |
| 5,360,429 A * | 11/1994 | Jeanson et al. ................. | 606/250 |
| 5,498,264 A | 3/1996 | Schlapfer et al. | |
| 5,507,745 A | 4/1996 | Logroscino et al. | |
| 5,520,689 A | 5/1996 | Schlapfer et al. | |
| 5,531,745 A | 7/1996 | Ray | |
| 5,542,946 A | 8/1996 | Logroscino et al. | |
| 5,545,164 A * | 8/1996 | Howland ..................... | 606/250 |
| 5,558,674 A | 9/1996 | Heggeness et al. | |
| 5,653,708 A | 8/1997 | Howland | |
| 5,665,089 A | 9/1997 | Dall | |
| 5,707,372 A | 1/1998 | Errico et al. | |
| 5,713,898 A | 2/1998 | Stucker et al. | |
| 5,928,233 A | 7/1999 | Apfelbaum | |

(Continued)

FOREIGN PATENT DOCUMENTS

EP    0 737 449    10/1996

(Continued)

OTHER PUBLICATIONS

Summit SI OCT Spinal Fixation System, 2 pages.

(Continued)

*Primary Examiner* — Thomas C. Barrett
*Assistant Examiner* — Matthew Lawson
(74) *Attorney, Agent, or Firm* — Sprinkle IP Law Group

(57) ABSTRACT

An occipital plate for use in an occipito-cervico-thoracic (OCT) construct is mounted to a patient's occipital bone. The occipital plate includes an elongate central section aligned with a midline of the base and a pair of angled sections that project away from the central section and include attachment assemblies for securing a rod to the occipital plate. The attachment assemblies have multi-adjustability features. At least a portion of the attachment assemblies is rotatable with respect to the base so that the rods may be coupled to the occipital plate at a variety of angles with respect to the midline. The angular adjustability may accommodate any misalignments in the rods. Additionally, the position of the attachment assemblies relative to the midline of the occipital plate is adjustable to thereby provide for medial-lateral adjustability when attaching the rods to the occipital plate as part of the OCT construct.

21 Claims, 4 Drawing Sheets

U.S. PATENT DOCUMENTS

| | | | |
|---|---|---|---|
| 5,976,135 A | 11/1999 | Sherman et al. | |
| 6,017,343 A | 1/2000 | Rogozinski | |
| 6,077,262 A | 6/2000 | Schlapfer et al. | |
| 6,096,040 A | 8/2000 | Esser | |
| 6,146,382 A | 11/2000 | Hurlbert | |
| 6,187,005 B1 | 2/2001 | Brace et al. | |
| 6,206,882 B1 | 3/2001 | Cohen | |
| 6,238,396 B1 | 5/2001 | Lombardo | |
| 6,296,644 B1 | 10/2001 | Saurat et al. | |
| 6,302,883 B1* | 10/2001 | Bono | 606/291 |
| 6,315,779 B1 | 11/2001 | Morrison | |
| 6,336,927 B2 | 1/2002 | Rogozinski | |
| 6,368,351 B1 | 4/2002 | Glenn et al. | |
| 6,379,358 B1 | 4/2002 | Kuo | |
| 6,432,109 B1 | 8/2002 | Letendart et al. | |
| 6,485,491 B1 | 11/2002 | Farris et al. | |
| 6,524,315 B1 | 2/2003 | Selvitelli | |
| 6,547,790 B2* | 4/2003 | Harkey et al. | 606/250 |
| 6,620,164 B2 | 9/2003 | Ueyama et al. | |
| 6,682,532 B2 | 1/2004 | Johnson | |
| 6,832,999 B2 | 12/2004 | Ueyama et al. | |
| 6,902,565 B2 | 6/2005 | Berger et al. | |
| 6,949,123 B2 | 9/2005 | Reiley | |
| 6,958,065 B2 | 10/2005 | Ueyama et al. | |
| 7,033,377 B2 | 4/2006 | Miller | |
| 7,060,069 B2 | 6/2006 | Kozak et al. | |
| 7,232,441 B2* | 6/2007 | Altarac et al. | 606/250 |
| 7,250,052 B2 | 7/2007 | Landry et al. | |
| 7,303,563 B2 | 12/2007 | Poyner et al. | |
| 7,491,218 B2 | 2/2009 | Landry | |
| 7,618,443 B2 | 11/2009 | Abdou | |
| 7,621,942 B2 | 11/2009 | Piehl | |
| 7,857,836 B2 | 12/2010 | Huebner | |
| 7,901,433 B2 | 3/2011 | Forton et al. | |
| 8,007,499 B2* | 8/2011 | Piehl | 606/71 |
| 2002/0049446 A1 | 4/2002 | Harkey, III et al. | |
| 2002/0120268 A1 | 8/2002 | Berger | |
| 2003/0004512 A1 | 1/2003 | Farris et al. | |
| 2003/0036759 A1 | 2/2003 | Musso | |
| 2003/0153913 A1* | 8/2003 | Altarac et al. | 606/61 |
| 2003/0163132 A1 | 8/2003 | Chin | |
| 2003/0176863 A1 | 9/2003 | Ueyama et al. | |
| 2004/0122426 A1 | 6/2004 | Michelson | |
| 2004/0127904 A1 | 7/2004 | Konieczynski et al. | |
| 2004/0153070 A1* | 8/2004 | Barker et al. | 606/61 |
| 2004/0172022 A1 | 9/2004 | Landry | |
| 2004/0267259 A1 | 12/2004 | Mazda | |
| 2005/0010227 A1 | 1/2005 | Paul | |
| 2005/0080417 A1 | 4/2005 | Alexis et al. | |
| 2005/0119656 A1 | 6/2005 | Ferrante et al. | |
| 2005/0124994 A1 | 6/2005 | Berger et al. | |
| 2005/0216005 A1 | 9/2005 | Howland | |
| 2005/0216008 A1 | 9/2005 | Zwirnmann | |
| 2005/0228382 A1 | 10/2005 | Richelsoph et al. | |
| 2005/0240185 A1* | 10/2005 | Boomer et al. | 606/69 |
| 2005/0251141 A1 | 11/2005 | Frigg et al. | |
| 2005/0273104 A1 | 12/2005 | Oepen et al. | |
| 2005/0277939 A1 | 12/2005 | Miller | |
| 2005/0283153 A1 | 12/2005 | Poyner et al. | |
| 2005/0288669 A1* | 12/2005 | Abdou | 606/61 |
| 2006/0004359 A1 | 1/2006 | Kramer et al. | |
| 2006/0004360 A1 | 1/2006 | Kramer et al. | |
| 2006/0004363 A1 | 1/2006 | Brockmeyer et al. | |
| 2006/0155283 A1 | 7/2006 | Doherty et al. | |
| 2006/0155284 A1* | 7/2006 | Doherty et al. | 606/69 |
| 2006/0184170 A1 | 8/2006 | Kapitan et al. | |
| 2006/0217710 A1* | 9/2006 | Abdou | 606/54 |
| 2006/0217723 A1 | 9/2006 | Suh | |
| 2006/0217724 A1 | 9/2006 | Suh | |
| 2006/0229610 A1* | 10/2006 | Piehl | 606/61 |
| 2006/0264932 A1 | 11/2006 | Bert | |
| 2007/0016189 A1 | 1/2007 | Lake | |
| 2007/0083201 A1 | 4/2007 | Jones et al. | |
| 2007/0118121 A1* | 5/2007 | Purcell et al. | 606/61 |
| 2007/0123872 A1 | 5/2007 | Brockmeyer et al. | |
| 2007/0299441 A1* | 12/2007 | Hoffman et al. | 606/61 |
| 2008/0051783 A1 | 2/2008 | Null et al. | |
| 2008/0086124 A1 | 4/2008 | Forton | |
| 2008/0147123 A1 | 6/2008 | Schermerhorn | |
| 2008/0177313 A1 | 7/2008 | Lemoine | |
| 2008/0177314 A1* | 7/2008 | Lemoine | 606/250 |
| 2008/0300635 A1 | 12/2008 | Lieponis | |
| 2009/0270924 A1 | 10/2009 | Wing et al. | |

FOREIGN PATENT DOCUMENTS

| | | |
|---|---|---|
| EP | 1180348 A | 12/2008 |
| FR | 2 687 561 | 2/1992 |
| FR | 2 760 629 | 3/1997 |
| WO | 9531147 | 11/1995 |
| WO | 9723170 | 7/1997 |
| WO | 9841160 | 9/1998 |
| WO | WO 2005122922 A2 | 12/2005 |
| WO | WO 2006019370 | 2/2006 |
| WO | WO 2006096756 | 9/2006 |
| WO | WO 2006102222 A2 | 9/2006 |
| WO | WO 2007044716 | 4/2007 |
| WO | WO 2006102222 A3 | 9/2007 |
| WO | WO 2007146482 | 12/2007 |
| WO | WO 2008042633 | 4/2008 |

OTHER PUBLICATIONS

Stryker Spine Products, "Products: Cervical OASYS" webpage, 1 page.
Blackstone Ascent, Production Information page, 1 page.
Interpore Cross International, "Introducing the Altrius OCT System", Biological & Structural Innovation, Copyright 2003, 2 pages.
Blackstone Medical Inc., "Ascent Posterior Occipital Cervico-Thoracic System", Cervical and Thoracolumbar Systems, Copyright 2005, 1 page.
Globus Medical, cervical webpage, 1 page.
Globus Medical, Protex CT . . . the new standard in OCT Stabilization systems, 1 page.
Depuy Spine, "Mountaineer OCT Spinal System", Copyright 2006, 6 pages.
Office Action issued in U.S. Appl. No. 11/085,672 mailed Nov. 17, 2006, Piehl, 9 pages.
Office Action issued in U.S. Appl. No. 11/085,672 mailed May 18, 2007, Piehl, 15 pages.
Office Action issued in U.S. Appl. No. 11/085,672 mailed Nov. 1, 2007, Piehl, 8 pages.
International Search Report and Written Opinion issued in PCT/US2007/066039, mailed Apr. 14, 2008, Zimmer Spine, Inc., 11 pages.
International Search Report and Written Opinion in PCT/US2007/079295 mailed Apr. 17, 2008, Abbott Laboratories, 14 pages.
Office Action issued in U.S. Appl. No. 11/085,672 mailed Apr. 29, 2008, Piehl, 9 pages.
Office Action issued in U.S. Appl. No. 11/423,201 mailed Sep. 3, 2008, Hoffman, 15 pages.
Office Action issued in U.S. Appl. No. 11/085,672 mailed Oct. 31, 2008, Piehl, 9 pages.
Office Action issued in U.S. Appl. No. 11/423,201 mailed Dec. 10, 2008, Hoffman, 17 pages.
International Preliminary Report on Patentability and Written Opinion issued in PCT/US2007/066039, mailed Dec. 10, 2008, Zimmer Spine, Inc., 6 pages.
Office Action issued in U.S. Appl. No. 11/423,201 mailed Mar. 5, 2009, Hoffman, 15 pages.
Office Action issued in U.S. Appl. No. 11/542,786 mailed Mar. 5, 2009, Forton, 7 pages.
Office Action issued in U.S. Appl. No. 11/085,672 mailed May 7, 2009, Piehl, 12 pages.
International Search Report and Written Opinion issued in PCT/US2006/009996 mailed Jul. 19, 2007, Zimmer Spine, Inc., 10 pages.
International Preliminary Report on Patentability issued in PCT/US2006/009996, mailed Sep. 25, 2007, Zimmer Spine, Inc., 8 pages.
International Preliminary Report on Patentability and Written Opinion issued in PCT/US2007/079295 mailed Apr. 7, 2009, Abbott Laboratories, 7 pages.
Office Action issued in U.S. Appl. No. 11/616,720 mailed May 27, 2009, Lemoine, 8 pages.

International Preliminary Report on Patentability, Chapter I, and Written Opinion issued in PCT/US2007/085190, mailed Jun. 30, 2009, Abbott Spine Inc., 8 pages.

International Search Report and Written Opinion, PCT/US2007/085190, mailed Jun. 3, 2008, 13 pages.

Office Action issued in U.S. Appl. No. 11/756,106 mailed Aug. 26, 2009, 7 pages.

Office Action issued in U.S. Appl. No. 11/542,786 mailed Sep. 30, 2009, 8 pgs.

Office Action issued in U.S. Appl. No. 11/616,720 mailed Dec. 24, 2009, 11 pgs.

Office Action issued in U.S. Appl. No. 11/756,106 mailed Feb. 19, 2010, 6 pgs.

Office Action issued in U.S. Appl. No. 11/542,786 mailed Mar. 15, 2010, 9 pgs.

Office Action issued in U.S. Appl. No. 11/616,720 mailed Jun. 10, 2010, 10 pgs.

Office Action issued in U.S. Appl. No. 11/756,106 mailed Sep. 1, 2010, 7 pgs.

Notice of Allowance issued in U.S. Appl. No. 11/542,786 mailed Aug. 26, 2010, 4 pgs.

Examination Report for European Patent Application No. 06738970.0, dated Oct. 21, 2010, European Patent Office, 7 pgs.

Office Action issued in U.S. Appl. No. 11/423,201 mailed Oct. 29, 2009, 11 pgs.

Office Action issued in U.S. Appl. No. 11/616,720 mailed Nov. 9, 2010, 11 pgs.

Office Action issued in U.S. Appl. No. 12/609,868 mailed Dec. 8, 2010, 16 pgs.

Office Action for U.S. Appl. No. 11/756,106 mailed Feb. 15, 2011, 8 pgs.

Notice of Allowance for U.S. Appl. No. 12/609,868, mailed Apr. 14, 2011, 8 pgs.

Office Action issued in U.S. Appl. No. 11/616,720 mailed Dec. 21, 2011, 12 pgs.

* cited by examiner

ADJUSTABLE OCCIPITAL PLATE

FIELD OF THE INVENTION

This invention relates generally to fixation devices used in orthopedic surgery. The invention relates more particularly to devices used for cervical posterior fixation utilizing a plate attached to a bone in the occipital region and secured to a rod which attaches to a cable, wire, plate, or screw fastened in the spinal region.

BACKGROUND OF THE INVENTION

Fixation devices are used in orthopedic surgery to stabilize bones such as those in the spinal column. One type of fixation device includes a plate attachable to a portion of a bone. The plate may be connected to another bone or another portion of the same bone, directly or through other connecting devices. For example, posterior fixation devices can include a plate fastened to the skull, or occiput, one or more rods running longitudinally along the spine and connected to the plate, and vertebral mounts such as plates, cables, wires, hooks, screws, or other connectors attached to a vertebra and connected to the rod.

A number of such mechanisms are known in the art. To accommodate the variation in patient size and anatomy, a plate often needs to be chosen from a set of plates of multiple sizes and/or varying geometry. This results in a higher cost of the assembly and a need to maintain separate inventory of the various size and geometry occiput plates. It also increases the surgical time because the surgeon must search for the device that best fits the patient. Moreover, in conventional mechanisms, to connect the rod or rods with the plate requires that the rods be precisely aligned with the connection features on the plate. Misalignment of the rods with the plates results in the surgeon making ad hoc adjustments to the device, which further increases the surgical time. Accordingly, there is a need for an improved fixation plate that reduces inventory and surgery duration while still providing a secure, reliable and robust connection between the rods and the occipital or other bone structure.

SUMMARY OF THE INVENTION

This invention addresses these and other shortcomings in the prior art. In one embodiment, the invention is directed to a fixation system for connecting a stabilizing system to a bone. More specifically, the invention in one embodiment is directed to an occipital plate for use in an occipito-cervico-thoracic (OCT) construct in which an occipital plate is mounted to a patient's occipital bone. Typically, a pair of rods is releasably secured in spaced relation to each other to the occipital plate and a number of vertebral mounts which may include plates, cables, wires, hooks, screws, or other connectors that secure the rods relative to specific vertebrae.

In one embodiment, the occipital plate includes a base with an elongate central section oriented with a midline of the base. A pair of angled sections extends from the central section on opposite sides of the midline and forms an angle with respect to the midline. The angled sections include attachment assemblies for securing one of the rods to the occipital plate. The attachment assemblies have multi-adjustability features. To this end, at least a portion of the attachment assemblies is rotatable with respect to the base so that the rods may be coupled to the occipital plate at a variety of angles with respect to the midline. In this way, the adjustability of the attachment assemblies may accommodate any misalignments in the rods. Additionally, the position of the attachment assemblies relative to the midline of the occipital plate is adjustable to thereby provide for medial-lateral adjustability when attaching the rods to the occipital plate as part of the OCT construct.

In specific embodiments, the attachment assemblies include a slide member which mates with the angled section of the occipital plate in a dove-tail joint configuration and a post extending from the slide member that receives a rod therein. A set screw is threadably coupled to the post to secure the rod relative to the attachment assembly and therefore to the occipital plate. The attachment assemblies may include an angle limiting mechanism that limits the range of angles through which the rotatable portion of the attachment assemblies may rotate relative to the occipital plate.

Therefore, as a result of this invention, a single occipital plate may be utilized for a variety of patient sizes and configurations and provides efficient and secure multi-adjustability, i.e., both angular adjustability and adjustability in a medial-lateral direction, when attaching the rods as part of an OCT construct.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
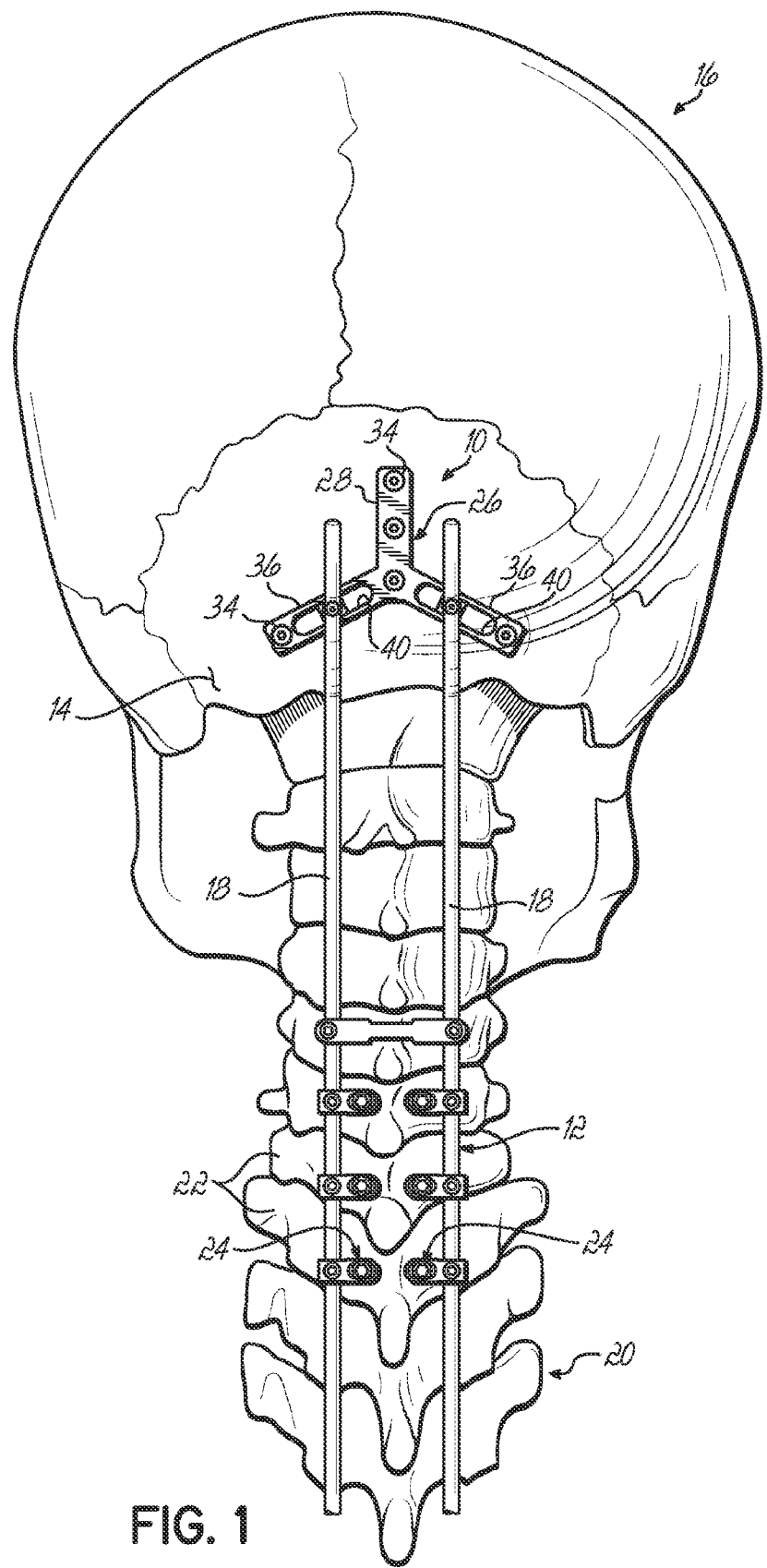
FIG. 1 is a posterior view of an exemplary occipito-cervico-thoracic construct utilizing an adjustable occipital plate according to one embodiment of the invention.

Referring to FIG. 1, one embodiment of an adjustable occipital plate 10 according to this invention is shown utilized as part of an occipito-cervico-thoracic (OCT) construct 12. The adjustable occipital plate 10 in FIG. 1 is mounted to the occipital bone 14 of a patient 16. One or more rods 18 are attached to the occipital plate 10 and run substantially along the spine 20 of the patient 16 and are attached to various segments of the spine 20 such as selected vertebrae 22 by vertebral mounts 24 according to any one of a know variety of such devices.

Figure 2:
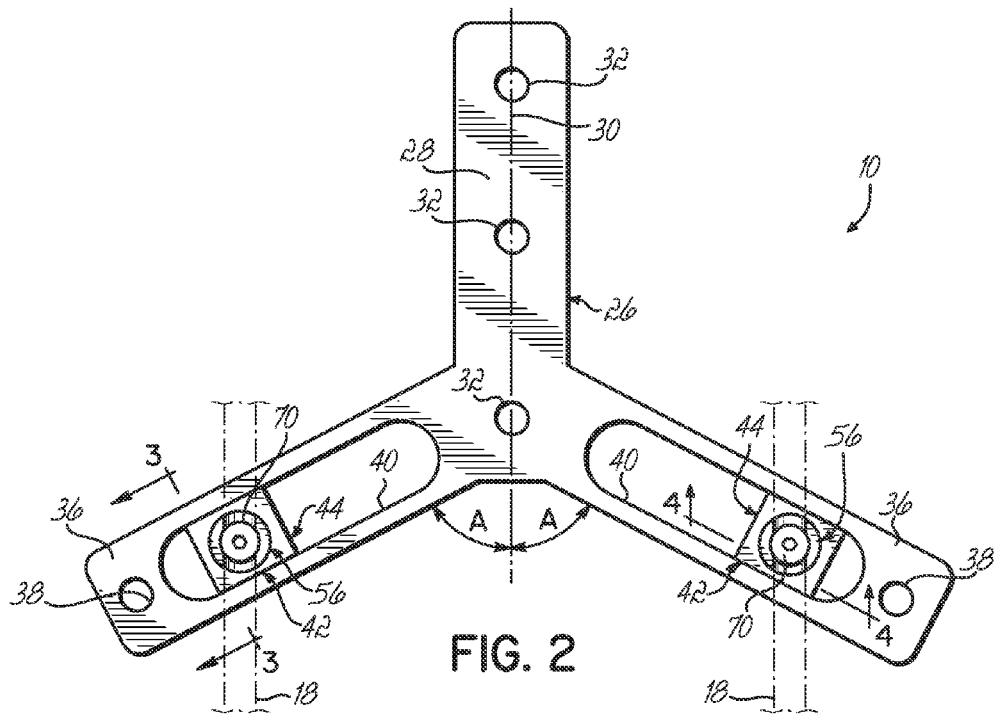
FIG. 2 is an exploded plan view of the components of one embodiment of the occipital plate according to this invention.

As shown in FIG. 2, the occipital plate 10 according to this embodiment of the invention includes a base plate 26 having an elongate central section 28 with a midline 30, which is generally aligned with the spine 20 when mounted to the occipital bone 14. The central section 28 may include a number of holes or apertures 32, three of which are shown, for bone screws 34 to mount the occipital plate 10 to the occipital bone 14 or another portion of the patient 16. The occipital plate 10 is generally symmetric relative to the midline 30 and includes a pair of angled sections 36 that at least have a component that projects laterally outward in opposite directions from the midline 30, i.e., in a direction that is at least in part perpendicular to the midline 30. In particular, the angled sections 36 form an angle A with respect to the midline 30. The angle A may be selected based on the specific application, but is generally between approximately 10° and approximately 90°, and more particularly between approximately 30° and approximately 70°. The invention, however, is not so limited as the angled sections 36 may be angled with respect to the midline 30 by an amount that provides a sufficient amount of lateral travel for connecting to rods 18 as is explained in more detail below. Each angled section 36 may include a hole or aperture 38 to receive a bone screw 34 there through for an additional mounting location to the occipital bone 14 or other bone.

As shown generally in FIG. 1 and more specifically in FIG. 2, the occipital plate 10 in accordance to one embodiment of this invention includes an elongate slot 40 formed in each of the angled sections 36 which extends substantially parallel to a length of its respective angled section 36. An attachment assembly, generally shown at 42, is mounted within the slot 40 and is capable of movement along the slot 40. Movement of the attachment assemblies 42 along slots 40 provides medial/lateral adjustability (i.e., in a direction substantially perpendicular to midline 30) of the attachment assembly 42 relative to the midline 30 of the central section 28 of the occipital plate 10 to allow for selective positioning of the rods 18 attached to the occipital plate 10 by the attachment assemblies 42. Depending on the angle A, movement of the attachment assemblies 42 along slots 40 may also provide a cephlad/caudal adjustability (i.e., in a direction substantially parallel to midline 30) of the attachment assemblies 42 that may be advantageous in some applications.

In one embodiment, each rod attachment assembly 42 includes a rectangular-shaped slide member 44 having an upper wall 46, a lower wall 48, and a pair of spaced apart sidewalls 50 projecting generally perpendicularly from the lower wall 48. Each of the sidewalls 50 includes an extension 52 projecting outwardly or away from the opposing sidewall 50. The spaced side edges of the slot 40 in each of the angled sections 36 of the base plate 26 each includes a rectangular-shaped groove 54 adapted to mate with one of the extensions 52 projecting from the sidewall 50 of the slide member 44, thereby forming a dove-tail joint construct between the attachment assembly 42 and the base plate 26. This dove-tail type of construction allows movement of the slide member 44 along slot 40 but limits movement of the slide member 44 in a direction substantially perpendicular to the slot 40. Thus, the slide member 44 is constrained to move along slot 40. The slide member 44 may be positioned in slot 40 in ways generally known in the art. For example, the terminating ends of angled sections 36 may be configured as end caps that allow the slide member 44 to be positioned in the slot 40 and which may subsequently be secured to the angled sections 36, such as by welding or other securing techniques, to retain the slide member 44 in the slot 40. Alternatively, the slide members 44 may be configured to elastically deform so as to allow the slide member 44 to be positioned in the slot 40. Once positioned in the slot 40, however, the slide member 44 returns to its non-deformed state and operates as described above.

Figure 3:
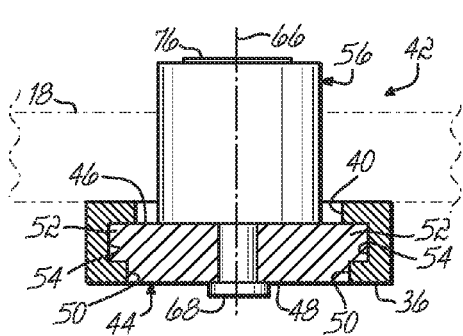
FIG. 3 is a cross-sectional view of the occipital plate shown in FIG. 2 generally taken along line 3-3.
Figure 4:
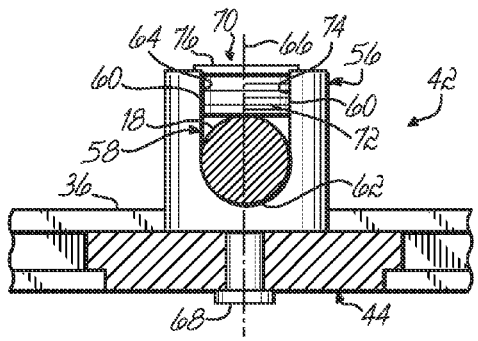
FIG. 4 is a cross-sectional view of the occipital plate shown in FIG. 2 generally taken along line 4-4.

In an exemplary embodiment, each slide member 44 includes a post 56 extending upwardly from the upper wall 46. Each post 56 includes a cavity 58 extending through the post 56 having a pair of spaced apart, generally straight sidewalls 60 and an arcuate lower wall 62. The cavity 58 further includes an opening 64 at an end opposite the arcuate lower wall 62 for receiving a rod 18 of the OCT construct 12. In this embodiment, the post 56 is not rigidly coupled to slide member 44, but instead is coupled so as to allow rotation of post 56 relative to slide member 44 about an axis 66 (FIGS. 3-4). For example, post 56 may be coupled to slide member 44 by a rivet 68. The invention, however, is not so limited as those of ordinary skill in the art will recognize other connectors that may be used to provide rotation of the post 56 relative to the slide member 44. The ability to rotate the posts 56 allows the surgeon to adjust the attachment assembly 42 so as to align the cavity 58 with the rods 18. In this way, any misalignment of the rods 18 may be compensated for through the rotation of the posts 56 thereby providing a more robust attachment between the rods 18 and the base plate 26 without significant time-consuming adjustments made by the surgeon.

The rod 18 is clamped to the attachment assembly 42, and as a result the occipital plate 10, by a set screw 70. The set screw 70 includes a threaded shaft 72 that is received in a threaded upper portion 74 of post 56. A head 76 of the set screw 70 sits atop the post 56. The head 76 of the set screw 70 includes a hex-shaped socket 78 to receive a wrench or other driver (not shown) to adjust the set screw 70 relative to the arcuate lower wall 62. The distal end of the shaft 72 of set screw 70 is juxtaposed against the upper side of rod 18 to secure the rod 18 to the attachment assembly 42. As such, the surgeon is able to secure the rod 18 relative to the midline 30 of the base plate 26 by setting the set screw 70.

Figure 5:
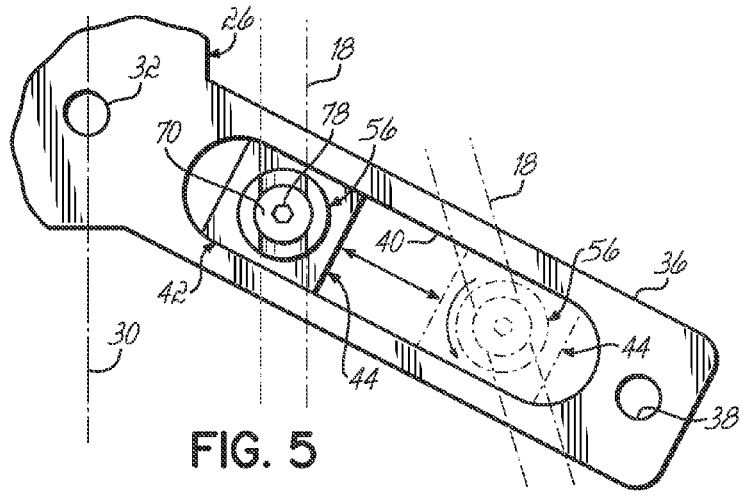
FIG. 5 is a partial exploded plan view of the occipital plate shown in FIG. 1 illustrating the adjustability of the attachment assembly shown in FIG. 1.

Therefore, the occipital plate 10 according to one embodiment of the invention provides for medial-lateral adjustability when attaching the rods 18 as part of an OCT construct 12. The occipital plate 10 also provides angular adjustability by permitting rotation of at least a portion of the attachment assembly 42 so as to accommodate any misalignment of the rods 18 with the attachment assembly 42. The surgeon only needs to tighten one set screw 70 for each attachment assembly 42 to lock the rod 18 relative to the midline 30 of the occipital plate 10. The adjustability of the attachment assembly 42 is illustrated in FIG. 5. For instance, the attachment assembly 42 is shown in one position (solid line) spaced a first distance from the midline 30 and adapted to receive a rod 18 in a first angular orientation. For illustrative purposes, the attachment assembly 42 is also shown in another position (phantom lines) spaced a second distance from the midline 30 and adapted to receive a rod 18 in a second angular orientation. The ability to adjust the medial-lateral distance from the midline 30 is a result of the slide member 44 moving along slot 40 in angled sections 36, and the ability to adjust to the angular orientation of the rod 18 is a result of the post 56 rotating relative to the slide member 44 so that the cavity 58 aligns with the rod 18. Such a multi-adjustability feature improves the use and functionality of attachment assembly 42 for OCT construct 12.

Other attachment assemblies and mechanisms can be utilized for securing the position of the rods 18 relative to the midline 30 of the occipital plate 10. For instance, FIGS. 6 and 7, in which like reference numerals refer to like features in FIGS. 1-5, illustrate an alternate attachment assembly in accordance with an embodiment of this invention. In particular, these figures show an attachment assembly 80 having a slide member 82 rigidly coupled to a post 84 extending from an upper surface of the slide member 82. The slide member 82 and post 84 may be integrally formed with each other or may be separate components that are rigidly affixed to each other through a subsequent assembly operation, such as by gluing, welding, and other processes known to those of ordinary skill in the art. Alternatively, the post 84 may rotate relative to slide member as described above.

The slide member 82 and post 84 each have a circular cross-sectional shape with the diameter of the post 84 being less than the diameter of the slide member 82 to define an annular flange 86 along the periphery of the slide member 82. In a manner similar to that shown in FIG. 3, the spaced side edges of each of the slots 40 in the angled sections 36 of base plate 26 each include a rectangular-shaped groove 54 (FIG. 3) adapted to mate with the annular flange 86 of the slide member 82. This type of construction allows movement of the slide member 82 along slot 40 but limits movement of the slide member 82 in a direction substantially perpendicular to the slot 40. Thus, the slide member 82 is constrained to move along slot 40. Moreover, due to the circular geometry of the slide member 82, the attachment assembly 80 is able to rotate within the slot 40 and relative to the base plate 26. For instance, when in the slot 40, the attachment assembly 80 can rotate relative to axis 66.

As in the previous embodiment, the post 84 includes a cavity 58 adapted to receive a rod 18, and further includes threaded upper portion 74 adapted to receive set screw 70 to clamp the rod 18 to the attachment assembly 80. The operation of attachment assembly 80 is similar to that described previously. An occipital plate 88 having an attachment assembly 80 also provides for medial-lateral adjustability when attaching the rods 18 as part of an OCT construct 12. The occipital plate 88 also provides angular adjustability by permitting rotation of the attachment assembly 80 so as to accommodate any misalignment of the rods 18 with the attachment assembly 80. Again, the surgeon only needs to tighten one set screw 70 for each attachment assembly 80 to lock the rod 18 relative to the midline 30 of the occipital plate 88.

Figure 7:
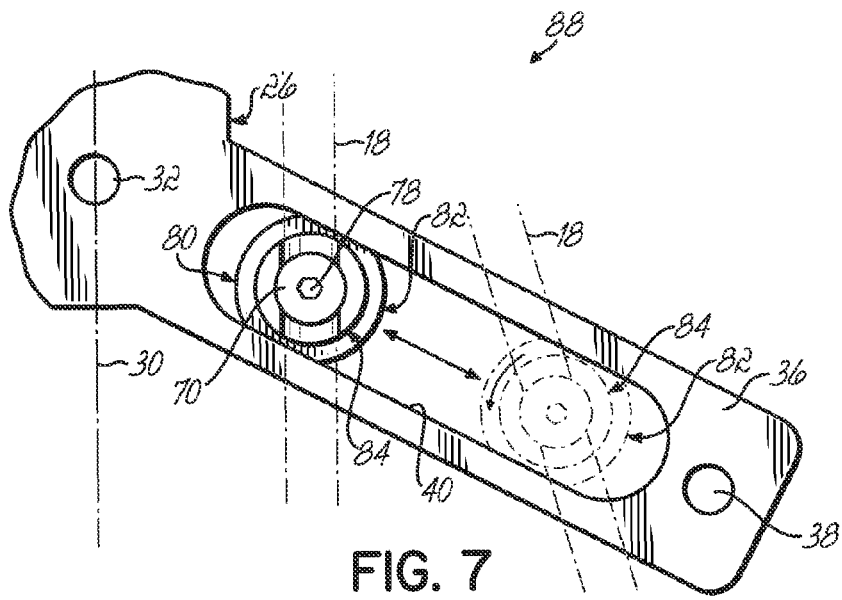
FIG. 7 is a partial exploded plan view of an occipital plate illustrating the adjustability of the attachment assembly shown in FIG. 6.

The adjustability of the attachment assembly 80 is illustrated in FIG. 7. The attachment assembly 80 is shown in one position (solid lines) spaced a first distance from the midline 30 and adapted to receive a rod 18 in a first angular orientation. For illustrative purposes, the attachment assembly 80 is also shown in another position (phantom lines) spaced a second distance from the midline 30 and adapted to receive a rod 18 in a second angular orientation. The ability to adjust the medial-lateral distance from the midline 30 is a result of the slide member 82 moving along slot 40 in angled sections 36, and the ability to adjust to the angular orientation of the rod 18 is a result of the attachment assembly 80 rotating relative to the base plate 26 so that the cavity 58 aligns with the rod 18. Thus, attachment assembly 80 also provides a multi-adjustability feature that improves the use and functionality of attachment assembly 80 for OCT construct 12.

Figure 8:
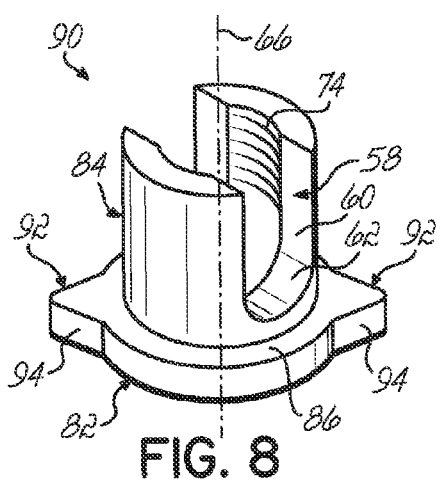
FIG. 8 is a perspective view of an attachment assembly according to another embodiment of the invention.
Figure 9:
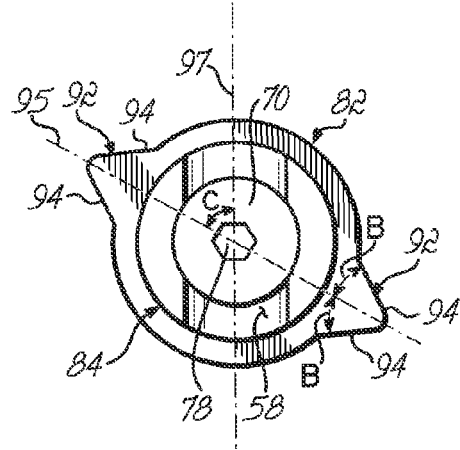
FIG. 9 is a plan view of the attachment assembly shown in FIG. 8.
Figure 10:
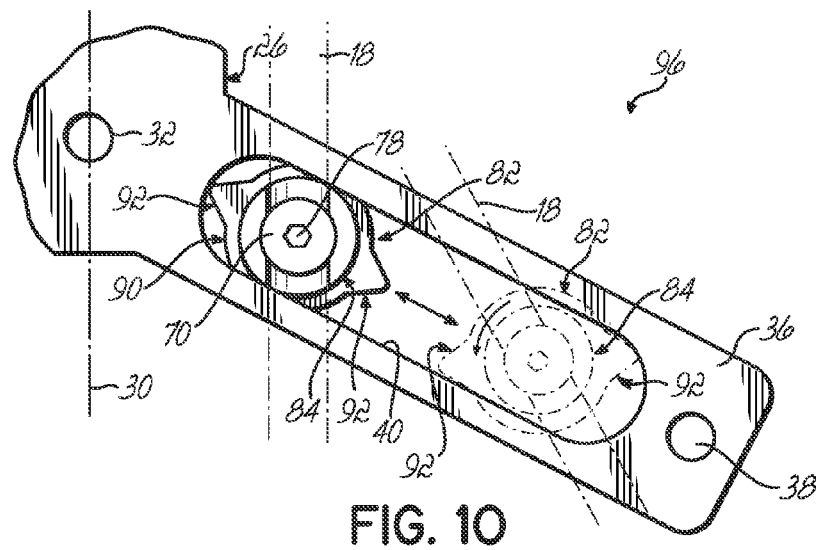
FIG. 10 is a partial exploded plan view of an occipital plate illustrating the adjustability of the attachment assembly shown in FIG. 8.

FIGS. 8-10, in which like reference numerals refer to like features in FIGS. 1-7, show yet another embodiment of an attachment assembly in accordance with an embodiment of this invention. In this embodiment, however, the range over which the attachment assembly or a portion thereof, may be rotated is limited. For instance, the embodiments shown and described in FIGS. 1-7 provide full rotation of the rotatable portion of the attachment assembly, i.e., the rotatable portion may rotate a full 360° within slot 40 In some applications, however, it may be desirable to limit the full range of rotation of the attachment assembly. Limiting the range of rotation may facilitate insertion of the rods 18 into their respective cavities in the attachment assemblies. For instance, depending on the range of rotation permitted, the attachment assemblies may operate so as to essentially self align with the rods as the rods are inserted into their respective cavities.

Figure 6:
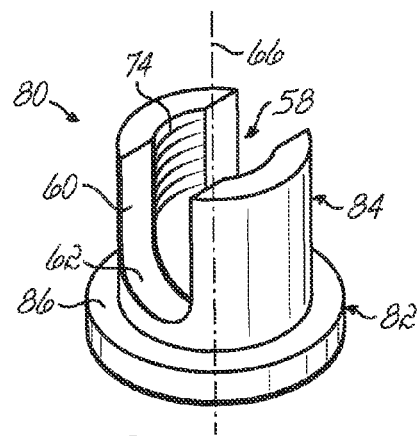
FIG. 6 is a perspective view of an attachment assembly according to another embodiment of the invention.

The embodiment of the attachment assembly 90 is similar in construction to the attachment assembly 80 shown in FIGS. 6 and 7 and described above. However, the attachment assembly 90 includes an angle limiting mechanism that limits the range of angles through which the rotatable portion of the attachment assembly rotates. In one embodiment, the angle limiting mechanism includes a pair of opposed triangularly-shaped wing members 92 projecting from the periphery of the slide member 82 so as to define a pair of bearing surfaces 94 for each of the wing members 92. The cross dimension between the apexes of the wing members 92 is greater than the width of the slot 40 along opposed grooves 54 in angled sections 36 (FIG. 3). The bearing surfaces 94 are angled with respect to an axis 95 (FIG. 9) by an angle B, which may control the amount of rotation of the attachment assembly 90 about the axis 66 when attachment assembly 90 is in slot 40. The rotation of the attachment assembly 90 is limited because a bearing surface 94 of opposed wing members 92 engages the wall of grooves 54 in slot 40. When the bearing surfaces 94 engage the grooves 54, further rotation in that particular direction (e.g., clockwise or counterclockwise) is prevented. By way of example, for an angle B of approximately 30°, the attachment assembly 90 may rotate about axis 66 for 30° in a clockwise direction, and 30° in a counterclockwise direction when the wing members 92 initially point along a direction generally parallel to the slot 40, as shown in solid in FIG. 10. The angle B may be between approximately 10° and approximately 40°, and more preferably approximately 30°. The invention, however, is not so limited as those of ordinary skill in the art may configure the wing members 92 to limit rotation of the attachment assembly 90 to a desired range.

As in the previous embodiment, the post 84 includes a cavity 58 adapted to receive a rod 18, and further includes threaded upper portion 74 adapted to receive set screw 70 to clamp the rod 18 to the attachment assembly 90. The operation of attachment assembly 90 is similar to that described previously. An occipital plate 96 having an attachment assembly 90 also provides for medial-lateral adjustability when attaching the rods 18 as part of an OCT construct 12. The occipital plate 96 also provides angular adjustability by permitting rotation of the attachment assembly 90 so as to accommodate any misalignment of the rods 18 with the attachment assembly 90. Unlike the previous embodiments, however, the rotation of attachment assembly 90 has a limited range due to the wing members 92 and their engagement with the grooves 54 in slots 40. Such a configuration may facilitate insertion of the rods 18 into the cavities 58 in posts 56. Again, the surgeon only needs to tighten one set screw 70 for each attachment assembly 90 to lock the rod 18 relative to the midline 30 of the occipital plate 96.

The adjustability of the attachment assembly 90 is illustrated in FIG. 10. The attachment assembly 90 is shown in one position (solid line) spaced a first distance from the midline 30 and adapted to receive a rod 18 in a first angular orientation. For illustrative purposes, the attachment assembly 90 is also shown in another position (phantom lines) spaced a second distance from the midline 30 and adapted to receive a rod 18 in a second angular orientation. The ability to adjust the medial-lateral distance from the midline 30 is a result of the slide member 82 moving along slot 40 in angled sections 36, and the ability to adjust to the angular orientation of the rod 18 is a result of the attachment assembly 90 rotating relative to the base plate 26 so that the cavity 58 aligns with the rod 18. Thus, attachment assembly 90 also provides a multi-adjustability feature that improves the use and functionality of attachment assembly 90 for OCT constructs 12.

In one aspect of the invention, as shown in FIG. 9, an axis 97 through cavity 58 in post 56 may be rotationally offset from axis 95 extending through the wing members 92 by an angle C. In one embodiment, the offset angle C is substantially equal to angle A. In this case, when the attachment assembly 90 is in slot 40 and axis 95 is substantially parallel to the slot 40, the axis 97 is substantially parallel to midline 30, and may receive a rod 18 that likewise is substantially parallel to midline 30. Such a configuration is shown in solid in FIG. 10. As explained above, the rods 18 may be misaligned so that the attachment assembly 90 must be rotated to align the cavity 58 with rod 18. Of course, the rods 18 may be misaligned such that either a clockwise rotation or a counterclockwise rotation is required to align the cavity 58 with the rod 18. To provide increased flexibility in accommodating misaligned rods, axis 97 should be parallel to midline 30 when axis 95 is parallel to the slot 40 to define a neutral angular position. In the neutral angular position, the attachment assembly 90 may rotate by approximately an equal amount in either the clockwise or counterclockwise direction, that amount being controlled by the angle B as previously discussed. By configuring the wing members 92 and cavity 58 in the manner dictated by the neutral angular position, the attachment assembly 90 is capable of accommodating misalignments of the rods by approximately an equal amount in either direction.

Figure 11:
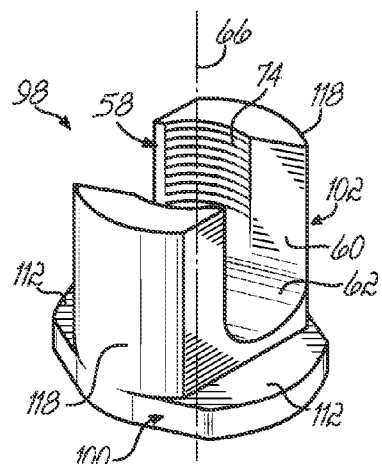
FIG. 11 is a perspective view of an attachment assembly according to another embodiment of the invention.
Figure 12:
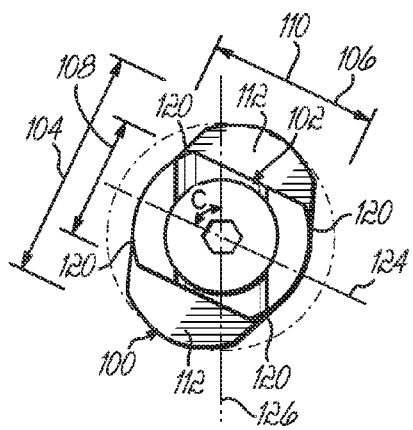
FIG. 12 is a plan view of the attachment assembly shown in FIG. 11.
Figure 13:
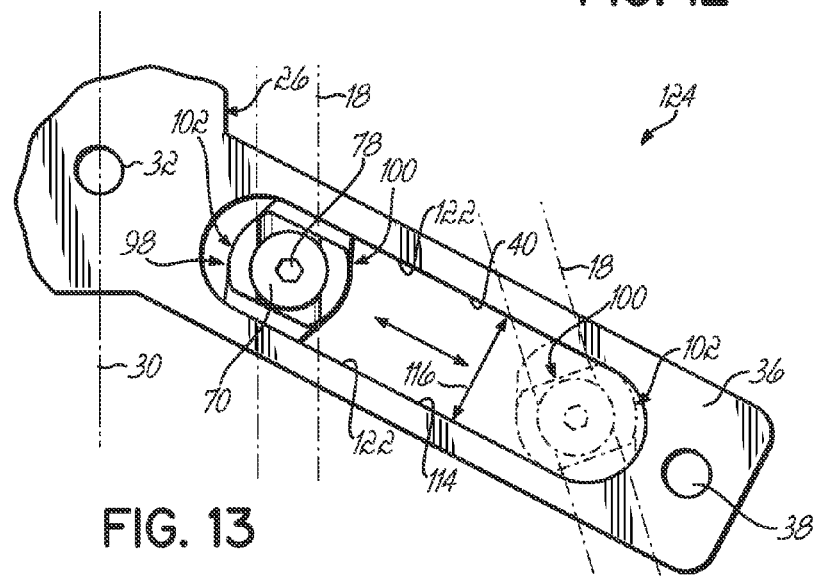
FIG. 13 is a partial exploded plan view of an occipital plate illustrating the adjustability of the attachment assembly shown in FIG. 11.

FIGS. 11-13, in which like reference numerals refer to like features in FIGS. 1-10, show yet another embodiment of an attachment assembly in accordance with an embodiment of this invention. In this embodiment, the range over which the attachment assembly may be rotated is again limited. As noted above, the limited range of rotation may facilitate insertion of the rods into the attachment assemblies and, depending on the range of rotation permitted, the attachment assemblies may operate so as to essentially self align with the rods as the rods are inserted into their respective cavities.

The embodiment of the attachment assembly 98 includes a slide member 100 rigidly coupled to a post 102 extending therefrom. As noted above, the slide member 100 and the post 102 may be integrally formed with each other or may be separate components that are rigidly affixed to each other. The slide member 100 is generally oblong having a first cross dimension 104 and a second cross dimension 106 that is less than the first cross dimension 104. In this embodiment the angle limiting mechanism is not associated with the slide member 100, but is instead associated with the post 102. Thus, material that would otherwise be used to form the slide member 100 may be removed (see phantom in FIG. 12). Such a design may reduce material costs and may provide additional advantages. The post 102 is also generally oblong in a direction 90° offset from that of the slide member 100. The post 102 has a first cross dimension 108 that is less than the first cross dimension 104 of the slide member 100 and a second cross dimension 110 that is approximately equal to the second cross dimension 106 of the slide member 100. Such a configuration defines a pair of opposed flanges 112. In a manner similar to that shown in FIG. 3, the spaced side edges of each of the slots 40 in the angled sections 36 of base plate 26 each include a rectangular-shaped groove 54 adapted to mate with one of the flanges 112 of slide member 100. The attachment assembly 98 may be positioned within slot 40 in a manner previously described. This type of construction allows movement of the slide member 100 along slot 40 but limits movement of the slide member 100 in a direction substantially perpendicular to the slot 40. Thus, the slide member 100 is constrained to move along slot 40. In addition, due to the geometry of the slide member 100, the slide member 100 is capable of rotating within slot 40 and relative to base plate 26 about axis 66. As discussed below, however, the rotation of the attachment assembly 98 is limited due to the interaction of the post 102 with the slot 40.

As shown in FIG. 13, the slot 40 in angled section 36 has an opening 114 with a cross dimension 116 that is greater than the first cross dimension 108 of the post 102 but is less than the second cross dimension 110 of the post 102. Thus, the post 102 fits within slot 40 when the long dimension of the post 102 (i.e., second cross dimension 110) is generally parallel with the slot 40, but does not fit within the slot 40 as the attachment assembly 98 is rotated. To this end, the outer surface 118 of the post 102 includes bearing surfaces 120 adapted to contact an inner edge 122 of opening 114 to limit the rotation of the attachment assembly 98 in both a clockwise and counterclockwise direction. Those of ordinary skill in the art will recognize how to vary or adjust the cross dimensions 108, 110 of the post 102 so as to achieve a desired range of rotation of the attachment assembly 98 relative to the base plate 26 when the attachment assembly 98 is in slot 40.

As in the previous embodiments, the post 102 includes a cavity 58 adapted to receive a rod 18, and further includes threaded upper portion 74 adapted to receive set screw 70 to clamp the rod 18 to the attachment assembly 98. The operation of attachment assembly 98 is similar to that described previously. An occipital plate 124 having an attachment assembly 98 also provides for medial-lateral adjustability when attaching the rods 18 as part of an OCT construct 12. The occipital plate 124 also provides angular adjustability by permitting rotation of the attachment assembly 98 so as to accommodate any misalignment of the rods 18 with the attachment assembly 98. Like the embodiment shown in FIGS. 8-10, the rotation of attachment assembly 98 has a limited range due to sizing of the post 102 and the engagement of the bearing surfaces 120 with the inner edges 122 in slot 40. Such a limited rotation configuration may facilitate insertion of the rods into the cavities 58. Again, the surgeon only needs to tighten one set screw 70 for each attachment assembly 98 to lock the rod 18 relative to the midline 30 of the occipital plate 124.

The adjustability of the attachment assembly 98 is illustrated in FIG. 13. The attachment assembly 98 is shown in one position (solid lines) spaced a first distance from the midline 30 and adapted to receive a rod 18 in a first angular orientation. For illustrative purposes, the attachment assembly 98 is also shown in another position (phantom lines) spaced a second distance from the midline 30 and adapted to receive a rod 18 in a second angular orientation. The ability to adjust the medial-lateral distance from the midline 30 is a result of the attachment assembly 98 moving along slot 40 in angled sections 36, and the ability to adjust to the angular orientation of the rod 18 is a result of the attachment assembly 98 rotating relative to the base plate 26 so that the cavity 58 aligns with the rod 18. Thus, attachment assembly 98 also provides a multi-adjustability feature that improves the use and functionality of attachment assembly 98 for OCT construct 12. In addition, the oblong configuration of slide member 100 also provides for a more efficient use of the length of slot 40. In other words, the attachment assembly 98 has an increased length of travel along slot 40 as compared to other designs due to the removal of material along the second cross dimension 106 of the slide member 100.

As shown in FIG. 12, an axis 124 through cavity 58 in post 56 may be rotationally offset from an axis 126 generally parallel to the long or second dimension of post 102 by an angle C. In one embodiment, the offset angle C is substantially equal to angle A. In this case, when the attachment assembly 98 is in slot 40 and axis 126 is substantially parallel to the slot 40, the axis 124 is substantially parallel to midline 30, and may receive a rod 18 that likewise is substantially parallel to midline 30. As explained above, the rods 18 may be misaligned so that the attachment assembly 98 must be rotated to align the cavity 58 with rod 18. Of course, the rods 18 may be misaligned such that either a clockwise rotation or a counterclockwise rotation is required to align the cavity 58 with the rod 18. To provide increased flexibility in accommodating misaligned rods, axis 124 should be parallel to midline 30 when axis 126 is parallel to the slot 40 to define a neutral angular position. In the neutral angular position, the attachment assembly 98 may rotate by approximately an equal amount in either the clockwise or counterclockwise direction.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. An occipital plate, comprising:
   a base plate having:
      an elongated central section with a midline; and
      a first section and a second section projecting laterally outward in opposite directions from the midline of the base plate, wherein the first section comprises a slot extending substantially parallel to a length of the first section; and
   an attachment assembly having:
      a slide member configured to move along the slot of the first section;
      a post coupled to the slide member, wherein the post has a first cross dimension and a second cross dimension wherein the first cross dimension of the post is less than a first cross dimension of the slide member and wherein the second cross dimension of the post is approximately equal to a second cross dimension of the slide member; and
      an angle limiting mechanism defining a range of rotation of the attachment assembly, wherein a medial-lateral distance between the attachment assembly and the midline of the base plate is adjustable relative to the angle along the slot of the first section, wherein at least a portion of the attachment assembly is rotatable after the slide member is positioned in the slot and coupled to the base plate, and wherein the angle limiting mechanism facilitates the attachment assembly to self-align or essentially self-align with a rod as the rod is received in an opening of the post of the attachment assembly.

2. The occipital plate of claim 1, wherein the second section comprises a slot extending substantially parallel to a length of the second section, further comprising:
   a second attachment assembly having a slide member constrained to move along the slot of the second section, wherein a medial-lateral distance between the second attachment assembly and the midline of the base plate is adjustable relative to the angle along the slot of the second section, and wherein at least a portion of the second attachment assembly is rotatable for angular orientation of a second rod coupled thereto relative to the midline of the base plate.

3. The occipital plate of claim 1, wherein the first section further comprises:
   a terminating end opposite of the midline of the base plate; and
   an aperture at the terminating end for receiving a bone screw therethrough.

4. The occipital plate of claim 1, wherein the first section further comprises:
   a terminating end opposite of the midline of the base plate, wherein the terminating end is configured to allow the slide member of the attachment assembly to be positioned in the slot of the first section; and
   an end cap configured to be secured to the terminating end to retain the slide member of the attachment assembly in the slot of the first section.

5. The occipital plate of claim 1, wherein the slide member of the attachment assembly is elastically deformable for positioning in the slot of the first section.

6. The occipital plate of claim 1, wherein the post is rotatable relative to the slide member about an axis extending through the post and the slide member.

7. The occipital plate of claim 1, wherein the attachment assembly further comprises a rivet, and wherein the post is coupled to the slide member via the rivet.

8. The occipital plate of claim 1, wherein the post is rigidly affixed to or integrally formed with the slide member.

9. The occipital plate of claim 1, wherein geometry of the slide member of the attachment assembly allows the slide member to rotate within the slot of the first section and relative to the base plate.

10. The occipital plate of claim 1, wherein the slide member is rotatable in the slot of the first section as permitted by the angle limiting mechanism.

11. The occipital plate of claim 10, wherein the angle limiting mechanism comprises at least one member projecting from a periphery of the slide member for engagement with the slot of the base member.

12. The occipital plate of claim 10, wherein the angle limiting mechanism is part of the post, wherein the post is rigidly affixed to or integrally formed with the slide member.

13. The occipital plate of claim 1, wherein the slot of the first section comprises a groove, wherein the slide member of the attachment assembly comprises a flange, and wherein the groove of the slot and the flange of the slide member mate to limit movement of the slide member of the attachment assembly in a direction substantially perpendicular to the slot of the first section.

14. The occipital plate of claim 1, wherein the angle is fixed.

15. The occipital plate of claim 1, wherein the angle between the first section and the midline of the base plate is between approximately 10° and approximately 90°.

16. The occipital plate of claim 15, wherein the angle between the first section and the midline of the base plate is between approximately 30° and approximately 70°.

17. The occipital plate of claim 1, wherein the angle limiting mechanism comprises a pair of triangularly-shaped wing members projecting from a periphery of the slide member.

18. The occipital plate of claim 17, wherein each of the triangularly-shaped wing members comprises bearing surfaces.

19. The occipital plate of claim 18, wherein the bearing surfaces are angled with respect to an axis by an angle B.

20. The occipital plate of claim 19, wherein the angle B controls an amount of rotation of the attachment assembly.

21. An occipital plate, comprising:
   a base plate having:
      an elongated central section with a midline; and
      a first section and a second section projecting laterally outward in opposing directions from the midline of the base plate, wherein the first section comprises:
         a slot extending substantially parallel to a length of the first section; and
         a groove formed on side edges of the slot; and
   an attachment assembly having:
      a slide member comprising at least one extension projecting from a periphery of the slide member to mate with the groove formed on the side edges of the slot so that a dove-tail joint construct is formed between the base plate and the attachment assembly; and
      a post coupled to the slide member, wherein the post has a first cross dimension and a second cross dimension, wherein the first cross dimension of the post is less than a first cross dimension of the slide member, and wherein the second cross dimension of the post is approximately equal to a second cross dimension of the slide member;
   wherein the slide member is constrained by the dove-tail joint construct to move along the slot of the first section, wherein a medial-lateral distance between the attachment assembly and the midline of the base plate is adjustable, wherein at least a portion of the attachment assembly is rotatable after the slide member is positioned in the slot and coupled to the base plate, and wherein the at least one extension of the slide member is configured to limit angular orientation of a rod coupled to the post of the attachment assembly to a range of angles relative to the midline of the base plate.

\* \* \* \* \*